United States Patent [19]

Kajander

[11] Patent Number: 5,171,238
[45] Date of Patent: Dec. 15, 1992

[54] ABSORBENT PAD WITH FIBROUS FACING SHEET

[75] Inventor: Richard E. Kajander, Ware, Mass.

[73] Assignee: The Transzonic Companies, Cleveland, Ohio

[21] Appl. No.: 324,411

[22] Filed: Mar. 16, 1989

[51] Int. Cl.⁵ ............................................. A61F 13/15
[52] U.S. Cl. .................................... 604/383; 604/378; 604/366
[58] Field of Search ............... 604/366, 370, 378, 383, 604/358

[56] References Cited

U.S. PATENT DOCUMENTS

| | | | |
|---|---|---|---|
| Re. 23,910 | 12/1954 | Smith et al. | 18/19 |
| 2,567,275 | 9/1951 | Colombo | 18/6 |
| 2,851,390 | 9/1958 | Chavannes | 154/125 |
| 2,896,626 | 7/1959 | Voigtman | 128/287 |
| 3,018,540 | 1/1962 | Chavannes | 29/148.4 |
| 3,047,444 | 7/1962 | Harwood | 154/46 |
| 3,056,406 | 10/1962 | Ness | 128/290 |
| 3,072,961 | 1/1963 | Gilbert | 18/10 |
| 3,073,304 | 1/1963 | Schaar | 128/156 |
| 3,088,463 | 5/1963 | Harmon | 128/290 |
| 3,205,112 | 9/1965 | Gilbert | 156/252 |
| 3,208,898 | 9/1965 | Chavannes et al. | 156/498 |
| 3,214,795 | 11/1965 | Hannauer, Jr. et al. | 18/10 |
| 3,221,738 | 12/1965 | Ekberg et al. | 128/287 |
| 3,243,488 | 3/1966 | Hannauer, Jr. et al. | 264/284 |
| 3,292,619 | 12/1966 | Egler | 128/156 |
| 3,294,091 | 12/1966 | Morse | 128/290 |
| 3,327,708 | 6/1967 | Sokolowski | 128/156 |
| 3,331,728 | 7/1967 | Lane | 161/112 |
| 3,344,789 | 10/1967 | Arnold et al. | 128/287 |
| 3,375,827 | 4/1968 | Bletzinger et al. | 128/290 |
| 3,399,672 | 9/1968 | Crowe, Jr. et al. | 128/156 |
| 3,416,523 | 12/1968 | Yeremian | 128/156 |
| 3,446,208 | 5/1969 | Fukuda | 128/156 |
| 3,482,567 | 12/1969 | Franklin | 128/132 |
| 3,485,705 | 12/1969 | Harmon | 161/59 |
| 3,536,563 | 10/1970 | Brandts et al. | 156/246 |
| 3,543,750 | 12/1970 | Meizanis | 128/156 |
| 3,545,442 | 12/1970 | Wicker et al. | 128/296 |
| 3,554,195 | 1/1971 | Murdoch | 128/284 |
| 3,639,199 | 2/1972 | Brandts et al. | 161/57 |
| 3,654,060 | 4/1972 | Goldman | 161/112 |
| 3,665,921 | 5/1972 | Stumpf | 128/287 |
| 3,674,221 | 7/1972 | Riemersma | 242/75.51 |
| 3,695,270 | 10/1972 | Dostal | 128/285 |
| 3,779,246 | 12/1973 | Mesek et al. | 128/287 |
| 3,811,445 | 5/1974 | Dostal | 128/285 |
| 3,814,101 | 6/1974 | Kozak | 128/287 |
| 3,837,773 | 9/1974 | Raley | 425/131 |
| 3,843,478 | 10/1974 | Zuscik | 161/164 |
| 3,849,050 | 11/1974 | Adams et al. | 425/363 |
| 3,881,489 | 5/1975 | Hartwell | 128/287 |
| 3,886,941 | 6/1975 | Duane et al. | 128/287 |
| 3,886,942 | 6/1975 | Bernardin | 128/290 |
| 3,888,248 | 6/1975 | Moore et al. | 128/156 |
| 3,894,827 | 7/1975 | Raley et al. | 425/363 |
| 3,908,659 | 9/1975 | Wehrmeyer et al. | 128/287 |
| 3,911,187 | 10/1975 | Raley | 428/180 |
| 3,916,447 | 11/1975 | Thompson | 2/46 |
| 3,929,135 | 12/1975 | Thompson | 128/287 |
| 3,945,386 | 3/1976 | Anczurowski et al. | 128/287 |
| 3,949,130 | 4/1976 | Sabee et al. | 428/192 |
| 3,950,480 | 4/1976 | Adams et al. | 264/284 |
| 3,957,414 | 5/1976 | Bussey, Jr. et al. | 425/384 |
| 3,965,906 | 6/1976 | Karami | 128/287 |
| 3,966,383 | 6/1976 | Bussey, Jr. et al. | 425/388 |
| 3,967,623 | 7/1976 | Butterworth et al. | 128/287 |

(List continued on next page.)

FOREIGN PATENT DOCUMENTS

| | | |
|---|---|---|
| 1138602 | 1/1984 | Canada . |
| 304617 | 9/1989 | European Pat. Off. . |
| 396108 | 11/1990 | European Pat. Off. . |
| 2409496 | 9/1975 | Fed. Rep. of Germany . |
| 2-227240 | 9/1990 | Japan . |

*Primary Examiner*—Randall L. Green
*Assistant Examiner*—R. Clarke
*Attorney, Agent, or Firm*—D. Peter Hochberg; Mark Kusner; Louis J. Weisz

[57] ABSTRACT

An absorbent pad, such as a sanitary napkin, is provided having a fibrous facing sheet. The fibrous face is a fractional-denier fibrous nonwoven fabric which may or may not be laminated to a thermoplastic sheet, depending on its strength. The sheet is vacuum perforated to make it permeable to body fluids.

21 Claims, 2 Drawing Sheets

U.S PATENT DOCUMENTS

| | | | |
|---|---|---|---|
| 3,989,867 | 11/1976 | Sisson | 428/132 |
| 3,994,299 | 11/1976 | Karami | 128/287 |
| 4,014,341 | 3/1977 | Karami | 128/287 |
| 4,041,951 | 8/1977 | Sanford | 128/287 |
| 4,077,410 | 3/1978 | Butterworth et al. | 128/287 |
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,184,902 | 1/1980 | Karami | 156/85 |
| 4,214,945 | 7/1980 | Lucas et al. | 156/634 |
| 4,233,017 | 11/1980 | Lucas et al. | 425/290 |
| 4,252,516 | 2/1981 | Raley et al. | 425/290 |
| 4,259,286 | 3/1981 | Louis et al. | 264/555 |
| 4,272,473 | 6/1981 | Riemersma et al. | 264/154 |
| 4,275,105 | 6/1981 | Boyd et al. | 428/198 |
| 4,282,874 | 8/1981 | Mesek | 128/287 |
| 4,287,251 | 9/1981 | King et al. | 428/198 |
| 4,323,068 | 4/1982 | Aziz | 128/287 |
| 4,324,246 | 4/1982 | Mullane et al. | 128/287 |
| 4,324,247 | 4/1982 | Aziz | 128/287 |
| 4,327,730 | 5/1982 | Sorensen | 128/287 |
| 4,341,216 | 7/1982 | Obenour | 128/287 |
| 4,341,217 | 7/1982 | Ferguson et al. | 128/290 W |
| 4,342,314 | 8/1982 | Radel et al. | 128/287 |
| 4,364,723 | 12/1982 | Louis et al. | 425/384 |
| 4,395,215 | 7/1983 | Bishop | 425/290 |
| 4,441,952 | 4/1984 | Mullane, Jr. | 156/222 |
| 4,463,045 | 7/1984 | Ahr et al. | 428/131 |
| 4,540,414 | 9/1985 | Wishman | 604/378 |
| 4,560,372 | 12/1985 | Pieniak | 604/369 |
| 4,578,069 | 3/1986 | Whitehead et al. | 604/370 |
| 4,585,449 | 4/1986 | Karami | 604/378 |
| 4,592,751 | 6/1986 | Gegelys | 604/368 |
| 4,622,036 | 11/1986 | Goodrum | 604/367 |
| 4,629,457 | 12/1986 | Ness | 604/382 |
| 4,704,112 | 11/1987 | Suzuki et al. | 604/378 |
| 4,726,976 | 2/1988 | Karami et al. | 604/366 |
| 4,735,843 | 4/1988 | Noda | 428/137 |
| 4,753,840 | 6/1988 | VanGompel | 604/366 |
| 4,755,413 | 7/1988 | Morris | 428/138 |
| 4,820,294 | 4/1989 | Morris | 604/383 |
| 4,872,870 | 10/1989 | Jackson | 604/366 |

ABSORBENT PAD WITH FIBROUS FACING SHEET

BACKGROUND OF THE INVENTION

This invention relates to absorbent pads that are worn against the body, such as sanitary napkins. More particularly, this invention relates to an absorbent pad having a facing sheet with a fractional-denier fibrous nonwoven surface facing the wearer's body.

Absorbent pads that are worn against the body for absorbing bodily fluids, such as sanitary napkins, disposable diapers, and surgical dressings, typically have an absorbent core, such as fluffed cellulose batting, surrounded by a cover sheet. The cover sheet maintains the integrity and shape of the pad, and typically includes a backsheet on the side away from the wearer that prevents escape of the fluids being absorbed by the core and a facing sheet or topsheet on the side facing the wearer.

The backsheet must be impervious to bodily fluids to prevent the escape of fluids if, e.g., the absorbent core becomes saturated or pressure is exerted on the core. Backsheets are thus typically sheets of plastic such as polyethylene or other polyolefins, although it is possible to provide a backsheet of a fibrous fabric—either woven or nonwoven—that is treated to make it impermeable.

The facing sheet must be permeable to whatever fluid is to be absorbed by the pad. Originally, such facing sheets were made from large-fiber (i.e., from about 1.0 to about 9.0 denier, and typically from about 1.0 to about 3.0 denier) nonwoven natural or synthetic fibers, and at one time even woven sheets were used, but such facing sheets can allow the fluid to escape back out of the pad, and onto the wearer's skin or clothing, if, e.g., the absorbent core becomes saturated or pressure is placed on the core.

More recently, cast thermoplastic facing sheets have been provided. The sheets—e.g., of polyethylene film—are perforated to allow the bodily fluids to enter the pad, but the perforations are said to be designed to trap the fluids in the pad. However, such thermoplastic sheets do not allow the wearer's skin to breathe, so that they allow the buildup of moisture from sweat, causing a clammy feeling or other discomfort or irritation. Therefore, it is known to give such thermoplastic facing sheets a textured or dimpled surface, forming a less film-like fabric, to reduce the surface area that touches the skin and thereby to reduce the clamminess and irritation. Nevertheless, such sheets are not as comfortable against the wearer's skin as a fibrous facing sheet.

It would be desirable to be able to provide a fibrous nonwoven facing sheet for a pad for absorbing bodily fluids that lacks the disadvantages of both large-fiber nonwoven fibrous sheets and non-fibrous thermoplastic sheets.

SUMMARY OF THE INVENTION

It is an object of this invention to provide a fibrous nonwoven facing sheet for a pad for absorbing bodily fluids that lacks the disadvantages of both large-fiber nonwoven fibrous sheets and non-fibrous thermoplastic sheets.

In accordance with this invention, there is provided an absorbent pad for absorbing bodily fluids. The pad comprises an inner core of absorbent material having a shape and size selected according to type and amount of bodily fluid to be absorbed and body location from which the fluids issue. The core has first and second sides. A fluid impermeable backsheet is adjacent one side of the core, and a fluid permeable facing sheet is adjacent a second side of the core for contacting the body location. The facing sheet comprises a hydrophobic nonwoven fibrous fabric having a soft surface and being perforated for contacting the body location. The facing sheet could be a laminate of a reinforcing thermoplastic sheet and the hydrophobic nonwoven fibrous fabric, the laminate being perforated, the thermoplastic sheet being adjacent the core and the nonwoven fabric facing outward for contacting the body location.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
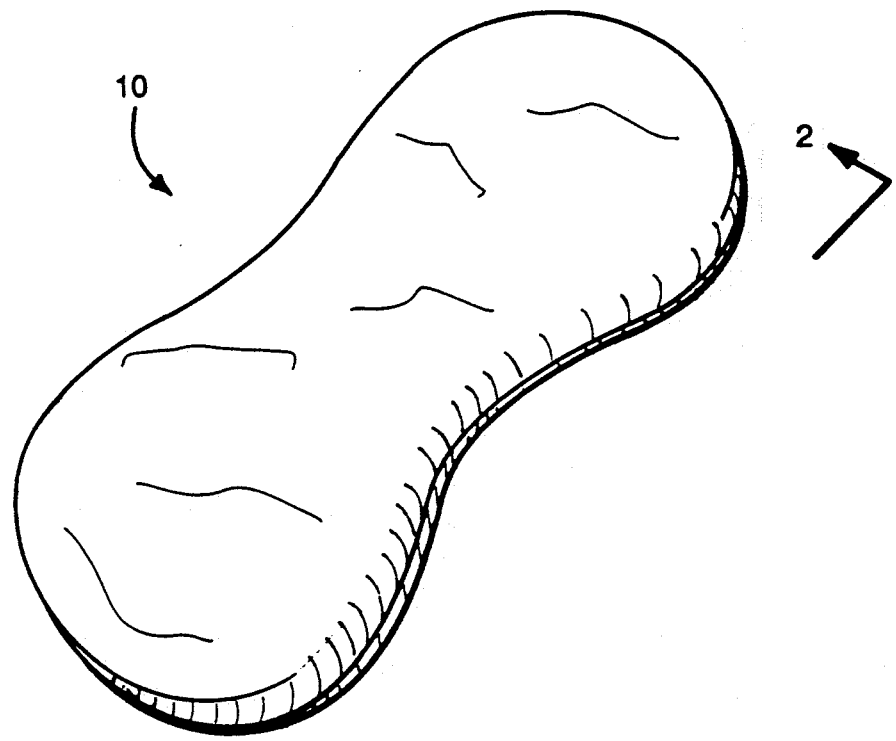
FIG. 1 is perspective view of an absorbent pad according to this invention.
Figure 2:
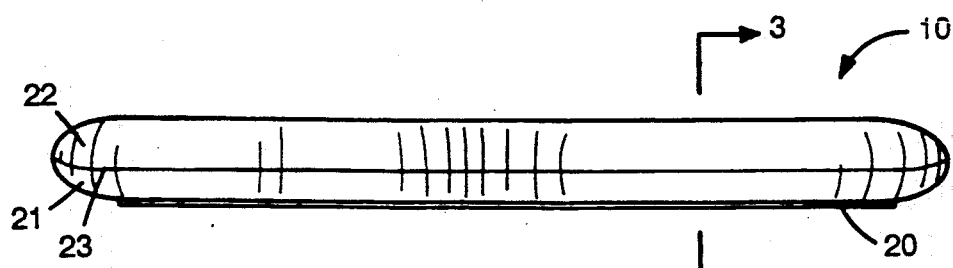
FIG. 2 is a side elevational view of an absorbent pad according to this invention, taken from line 2—2 of FIG. 1.
Figure 3:
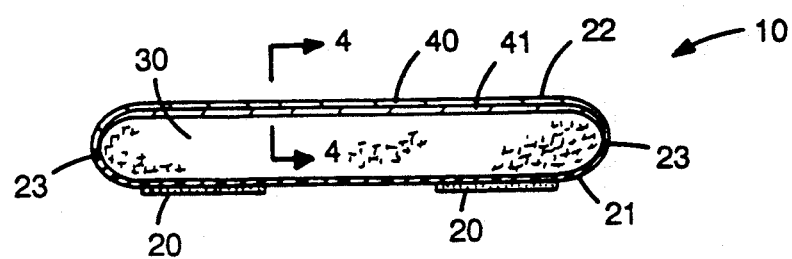
FIG. 3 is a cross-sectional view of an absorbent pad according to this invention, taken from line 3—3 of FIG. 2.
Figure 4:
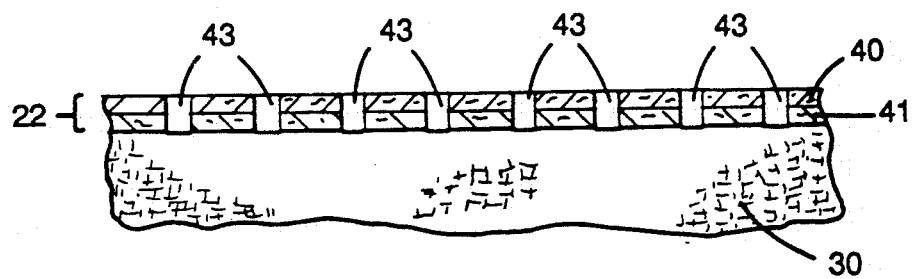
FIG. 4 is a cross-sectional view of a laminated facing sheet according to this invention, taken from line 4—4 of FIG. 3.

An absorbent pad according to this invention is illustated as a sanitary napkin 10 in FIGS. 1-4, although the invention applies to all types of absorbent pads that are worn against the body, such as, e.g., diapers. Sanitary napkin 10 is worn in the crotch of a woman's underpants, attached by adhesive bands 20. Sanitary napkin 10 has an absorbent core 30, which may be of fluffed cellulose batting or any other suitable material. Core 30 is surrounded by a cover sheet made up of backsheet 21 and topsheet 22. Typically both backsheet 21 and topsheet 22 would be of thermoplastic material and they would be fused together by the application of heat at seam 23. However, it is possible that one or both of backsheet 21 and topsheet 22 would not be thermoplastic, in which case an alternative means of fastening and sealing the two layers might be necessary.

The purpose of backsheet 21 is to keep fluids, such as menstrual fluids, that are absorbed by core 30 from escaping to soil the wearer or the wearer's clothing. Such fluids might be released from core 30, e.g., if core 30 were somehow compressed. Backsheet 21 is therefore fluid impermeable. Backsheet 21 is preferably a solid sheet of a thermoplastic material such as polyethylene, although a nonwoven fibrous material treated to resist the passage of fluids would suffice. Of course, other polyolefins, or other thermoplastic materials, could be used to form backsheet 21.

Unlike backsheet 21, topsheet 22 must allow the passage of fluids into core 30. However, for the comfort of the wearer, topsheet 22 preferably has a fibrous surface In a preferred embodiment, at least the surface of topsheet 22 is a fractional-denier (i.e., significantly less than 1 denier) fibrous nonwoven polypropylene web 40, which is formed by blowing polypropylene through a spinneret to produce microfibers (i.e., fibers of less than 1.0 denier having a diameter less than about 15 microns and preferably between about 0.5 micron and about 5 microns) which interlock with one another without adhesion, as by tangling, to form a nonwoven fibrous fabric mat. Alternately, electrostatic, air-assisted, or other techniques could be used to create the non-woven web. Preferably, the melt blown web 40 is a microfiber melt blown web having a basis weight of between about 0.15 oz./yd.² and about 1.5 oz./yd.² and more preferably between about 0.25 oz./yd.² and about 0.7 oz./yd.². Of course, other polyolefins, or other thermoplastic materials, could be used to form web 40.

In a first preferred embodiment, web 40 alone forms top sheet 22. However, depending on its basis weight and other characteristics of its fibers, such as fiber diameter, degree of entanglement, fiber (polymer) stretch, and fiber alignment, web 40 may not be strong enough to serve alone as topsheet 22 without unacceptable risk of tearing. If web 40 is not strong enough on its own, then, according to a second preferred embodiment of the invention, it is laminated with a reinforcing sheet 41 of a suitable material such as polyethylene, another polyolefin, or other thermoplastic material. The laminate can be formed by heating each layer 40, 41 to soften them and then bringing them together so that they adhere to one another. Alternatively, fractional-denier fibrous web 40 can be laid down directly on softened reinforcing sheet 41 as web 40 is formed. According to this alternative, sheet 41 can have been formed previously and softened by heating, or can have been formed contemporaneously with web 40 so that it has not completely hardened by the time web 40 is laid down on it. In any case, the thickness of sheet 41 should be kept to a minimum necessary to provide the required strength Preferably, sheet 41 should be about 0.0008 inch thick, while web 40 should have a basis weight of about 20 g/m² if a laminate is used, or a basis weight of about 20 g/m² to about 40 g/m² if it is used alone.

Whether topsheet 22 is a laminate, or consists of fractional-denier fibrous web 40 alone, it must be permeable to fluids in order to function. If it consists of fractional-denier fibrous web 40 alone, it may or may not be sufficiently permeable without more, but if it is a laminate, sheet 41 will prevent it from being permeable. Therefore, in accordance with this invention, topsheet 22 is provided with perforations 43. Perforations 43 are preferably deep-drawn straight-walled or irregular channels that trap fluids inside pad 10. Perforations 43 are preferably between about 0.010 inch and about 0.022 inch deep, and preferably between about 0.013 inch and about 0.019 inch deep in order to trap fluid within pad 10. Perforations 43 can be made by any suitable technique; however, vacuum perforation is preferred.

In yet another embodiment, sheet 41 can be formed and perforated before web 40 is laid down on it. In such an embodiment, the pre-perforated sheet 41 might be softened by heating, as above, to receive the fibers of web 40. The characteristics of topsheet 22 (including web 40, sheet 41, and perforations 43) would be the same as above.

Thus it seen that a pad for absorbing bodily fluids is provided having a facing sheet that lacks the disadvantages of both large-fiber nonwoven fibrous sheets and nonfibrous thermoplastic sheets. One skilled in the art will appreciate that the present invention can be practiced by other than the described embodiments, which are presented for purposes of illustration and not of limitation, and the present invention is limited only by the claims which follow.

What is claimed is:

1. An absorbent pad for absorbing bodily fluids, said pad comprising:
    an inner core of absorbent material having a shape and size selected according to type and amount to bodily fluid to be absorbed and body location from which the fluids issue, said core having first and second sides;
    a fluid impermeable backsheet adjacent one side of said core; and
    a fluid permeable facing sheet adjacent a second side of said core for contacting said body location, said facing sheet being a laminate of a reinforcing thermoplastic sheet and a hydrophobic nonwoven fibrous fractional-denier microfiber web having a soft surface, fibers with a diameter less than about 15 microns which interlock with one another, without adhesion, to form the nonwoven fibrous web, and a basis weight of between about 0.15 oz/yd² and about 1.5 oz/yd², said laminate being provided with a plurality of perforations (other than inter-fiber spaces) for facilitating passage of fluid into said pad, said thermoplastic sheet being adjacent said core and said nonwoven fabric facing outward for contacting said body location.

2. The pad of claim 1 wherein said reinforcing thermoplastic sheet is made from a material that is impermeable.

3. The pad of claim 2 wherein said impermeable material is a polyolefin.

4. The pad of claim 3 wherein said polyolefin is polyethylene.

5. The pad of claim 1 wherein said nonwoven fabric is a fractional-denier microfiber web having fibers with a diameter between about 0.5 micron and about 5 microns.

6. The pad of claim 1 wherein said web has a basis weight between about 0.25 oz./yd.² and about 0.7 oz.-/yd.².

7. The pad of claim 1 wherein said nonwoven fabric is a fractional-denier fibrous web of a polyolefin.

8. The pad of claim 7 wherein said polyolefin is polypropylene.

9. The pad of claim 1 wherein said perforated laminate has a plurality of deep-drawn holes therein, each of said deep-drawn holes being between about 0.010 inch and about 0.022 inch deep.

10. The pad of claim 9 wherein each of said deep-drawn holes has a depth between about 0.013 inch and 0.019 inch.

11. An absorbent pad for absorbing bodily fluids, said pad comprising:
    an inner core of absorbent material having a shape and size selected according to type and amount of bodily fluid to be absorbed and body location from which the fluids issue, said core having first and second sides;
    a fluid impermeable backsheet adjacent one side of said core; and
    a fluid permeable facing sheet adjacent a second side of said core for contacting said body location, said facing sheet comprising a hydrophobic nonwoven fibrous fractional-denier microfiber web having a soft surface, fibers with a diameter less than about 15 microns which interlock with one another, without adhesion, to form the nonwoven fibrous web, and a basis weight of between about 0.15 oz/yd² and about 1.5 oz/yd², said facing sheet being provided with a plurality of perforations (other than inter-fiber spaces) for facilitating passage of fluid into said pad, said nonwoven fabric being for contacting said body location.

12. The pad of claim 11 wherein said facing sheet is a laminate of a reinforcing thermoplastic sheet and said nonwoven fabric, said laminate being provided with said plurality of perforations (other than inter-fiber spaces) for facilitating passage of fluid into said pad, said thermoplastic sheet being adjacent said core and said nonwoven fabric facing outward for contacting said body location.

13. The pad of claim 12 wherein said reinforcing thermoplastic sheet is made from a material that is impermeable.

14. The pad of claim 13 wherein said impermeable material is a polyolefin.

15. The pad of claim 14 wherein said polyolefin is polyethylene.

16. The pad of claim 11 wherein said nonwoven fabric is a fractional-denier microfiber web having fibers with a diameter between about 0.5 micron and 5 microns.

17. The pad of claim 11 wherein said web has a basis weight between about 0.25 oz.yd.² and 0.7 oz./yd.².

18. The pad of claim 11 wherein said non-woven fabric is a fractional-denier fibrous web of a polyolefin.

19. The pad of claim 18 wherein said polyolefin is polypropylene.

20. The pad of claim 11 wherein said perforated facing sheet has a plurality of deep-drawn holes therein, each of said deep-drawn holes being between about 0.010 inch deep and about 0.022 inch deep.

21. The pad of claim 20 wherein each of said deep-drawn holes has a depth between about 0.013 inch and 0.019 inch.

* * * * *

UNITED STATES PATENT AND TRADEMARK OFFICE
CERTIFICATE OF CORRECTION

PATENT NO. : 5,171,238

DATED : December 15, 1992

INVENTOR(S) : Richard E. Kajander

It is certified that error appears in the above-identified patent and that said Letters Patent is hereby corrected as shown below:

On the title page:

Item 73 (Assignee): The Tranzonic Companies

Signed and Sealed this

Seventh Day of December, 1993

*Attest:*

BRUCE LEHMAN

*Attesting Officer*   *Commissioner of Patents and Trademarks*